(12) United States Patent
Casey et al.

(10) Patent No.: US 9,557,257 B2
(45) Date of Patent: Jan. 31, 2017

(54) VIBRATING DENSITOMETER WITH AN IMPROVED VIBRATING MEMBER

(71) Applicant: Micro Motion, Inc., Boulder, CO (US)

(72) Inventors: Megan Casey, Boulder, CO (US); Anthony William Pankratz, Arvada, CO (US)

(73) Assignee: Micro Motion, Inc., Boulder, CO (US)

( * ) Notice: Subject to any disclaimer, the term of this patent is extended or adjusted under 35 U.S.C. 154(b) by 157 days.

(21) Appl. No.: 14/425,565

(22) PCT Filed: Sep. 26, 2012

(86) PCT No.: PCT/US2012/057330
§ 371 (c)(1),
(2) Date: Mar. 3, 2015

(87) PCT Pub. No.: WO2014/051574
PCT Pub. Date: Apr. 3, 2014

(65) Prior Publication Data
US 2015/0219540 A1    Aug. 6, 2015

(51) Int. Cl.
*G01N 9/00* (2006.01)
*G01N 9/36* (2006.01)
*G01N 19/00* (2006.01)
*G01N 33/00* (2006.01)

(52) U.S. Cl.
CPC .............. *G01N 9/36* (2013.01); *G01N 9/002* (2013.01); *G01N 19/00* (2013.01); *G01N 33/0004* (2013.01); *G01N 2009/006* (2013.01)

(58) Field of Classification Search
CPC ...................................................... G01N 9/002
See application file for complete search history.

(56) References Cited

U.S. PATENT DOCUMENTS

| 3,874,221 A * | 4/1975 | Lockie | ................... G01N 9/002 374/117 |
| 5,373,745 A | 12/1994 | Cage | |
| 2015/0219540 A1* | 8/2015 | Casey | ................... G01N 9/002 73/24.05 |

FOREIGN PATENT DOCUMENTS

| DE | 4034883 A1 | 5/1992 |
| EP | 0222503 A1 | 5/1987 |
| RU | 2010129445 A | 1/2012 |
| WO | 2009078880 A1 | 6/2009 |
| WO | 2012030353 A2 | 3/2012 |

* cited by examiner

*Primary Examiner* — Laura Martin
*Assistant Examiner* — Alex Devito
(74) *Attorney, Agent, or Firm* — The Ollila Law Group LLC (57) ABSTRACT

A vibrating member (500) for a vibrating densitometer (800) is provided. The vibrating member (500) includes an inner surface (531) with one or more arcuate portions (730). The inner surface (531) of the vibrating member (500) also includes one or more raised portions (530) sized and located to increase a frequency separation between a resonant frequency of a desired vibrational drive mode and a resonant frequency of one or more undesired vibrational modes.

18 Claims, 7 Drawing Sheets

FIG. 8

VIBRATING DENSITOMETER WITH AN IMPROVED VIBRATING MEMBER

TECHNICAL FIELD

The embodiments described below relate to, vibrating densitometers, and more particularly, to a vibrating densitometer with a vibrating member for a vibrating densitometer having improved vibrational mode separation.

BACKGROUND OF THE INVENTION

Densitometers are generally known in the art and are used to measure a density of a fluid. The fluid may comprise a liquid, a gas, a liquid with suspended particulates and/or entrained gas, or a combination thereof. While there are various types of densitometers that operate according to different principles, one type of densitometer that has received great commercial success is a vibrating densitometer. Vibrating densitometers can comprise a vibrating member, such as a cylinder, a conduit, a pipe, a tube, etc. that is exposed to a fluid under test. One example of a vibrating densitometer comprises a conduit cantilever mounted with an inlet end coupled to an existing pipeline or other structure and the outlet end free to vibrate. Alternatively, both the inlet and outlet may be fixed with the portion of the conduit between the inlet and outlet vibrating. The conduit can be vibrated at resonance and the resonant frequency can be measured. As is generally known in the art, the density of the fluid under test can be determined by measuring the reduced resonant frequency of the conduit. According to well-known principles, the resonant frequency of the conduit will vary inversely with the density of the fluid that contacts the conduit. Therefore, while some vibrating densitometers are capable of measuring a density of a liquid, viscous damping caused by the liquid on the outside of the cylinder can reduce the measurement capabilities of vibrating densitometers. Liquid vibrating densitometers thus use vibrating pipes or tubes that have the fluid only on the inside, while gas vibrating densitometers typically are immersed in the fluid, having gas both on the inside and the outside of the cylinder. Therefore, typically, vibrating densitometers are used to measure a density of a gas.

Figure 1:
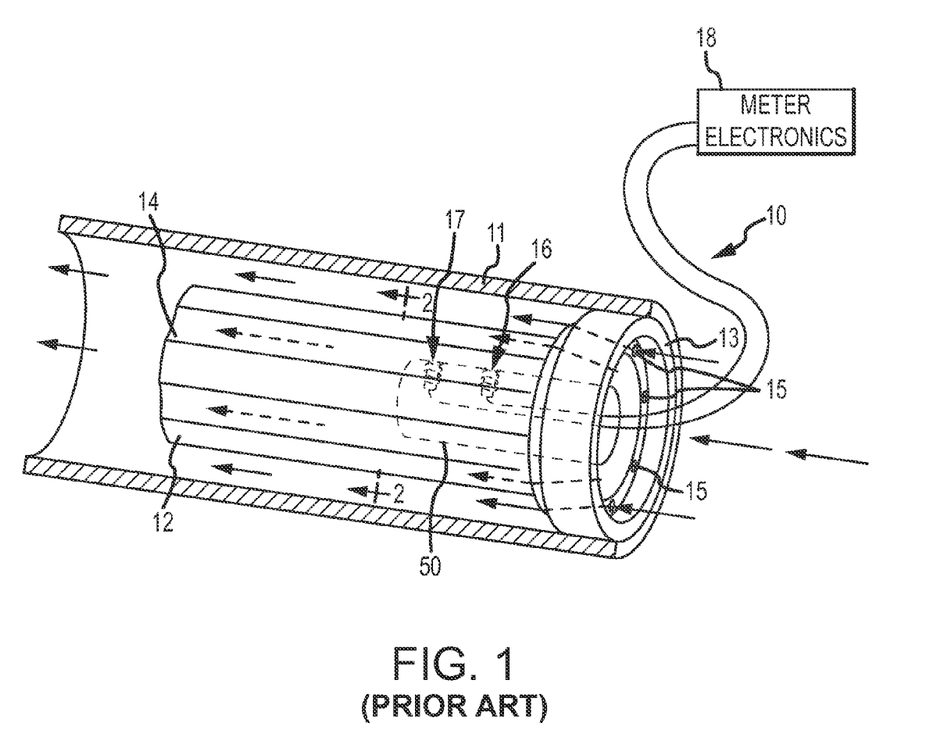
FIG. 1 shows a prior art vibrating densitometer.

FIG. 1 shows a prior art immersed densitometer 10. The prior art densitometer 10 may be configured to measure a density of a fluid, such as a liquid or a gas, for example. The densitometer 10 includes a housing 11 with a vibrating member 12 located at least partially within the housing 11. A portion of the housing 11 is cut away to show the vibrating member 12. The densitometer 10 may be placed in-line in an existing pipeline, for example. Alternatively, the housing 11 may comprise closed ends with apertures to receive a fluid sample, for example. Therefore, while flanges are not shown, in many instances, the housing 11 or the vibrating member 12 may include flanges or other members for operatively coupling the densitometer 10 to a pipeline or similar fluid delivering device in a fluid-tight manner. According to the example shown, the vibrating member 12 is cantilever mounted to the housing 11. The vibrating member 12 is shown coupled to the housing 11 at an inlet end 13 with the outlet end 14 free to vibrate.

According to the example shown, the vibrating member 12 also includes a plurality of fluid apertures 15 near the inlet end 13. The fluid apertures 15 can be provided to allow some of the fluid entering the densitometer 10 to flow between the housing 11 and the vibrating member 12. Therefore, the fluid contacts the inside as well as the outside surfaces of the vibrating member 12. This is particularly helpful when the fluid under test comprises a gas because a greater surface area is exposed to the gas. In other examples, apertures may be provided in the housing 11 to expose the fluid under test to the outer surface of the vibrating member 12 and therefore, the apertures 15 are not required in the vibrating member 12.

Further shown in FIG. 1 is a driver 16 and a vibrating sensor 17 positioned within a cylinder 50. The driver 16 and vibrating sensor 17 are shown as comprising magnet/coil combinations, which are well known in the art. If an electric current is provided to the coil, a magnetic field is induced in the vibrating member 12 causing the vibrating member 12 to vibrate. Conversely, the vibration of the vibrating member 12 induces a voltage in the vibrating sensor 17. The driver 16 receives a drive signal from a meter electronics 18 in order to vibrate the vibrating member 12 at one of its resonant frequencies in one of a plurality of vibration modes, including for example simple bending, torsional, radial, or coupled type. The vibrating sensor 17 detects the vibration of the vibrating member 12, including the frequency at which the vibrating member 12 is vibrating and sends the vibration information to the meter electronics 18 for processing. As the vibrating member 12 vibrates, the fluid contacting the vibrating member's wall vibrates along with the vibrating member 12. The added mass of the fluid contacting the vibrating member 12 lowers the resonant frequency. The new, lower, resonant frequency of the vibrating member 12 is used to determine the density of the fluid as is generally known in the art according to a previously determined correlation, for example.

Figure 3:
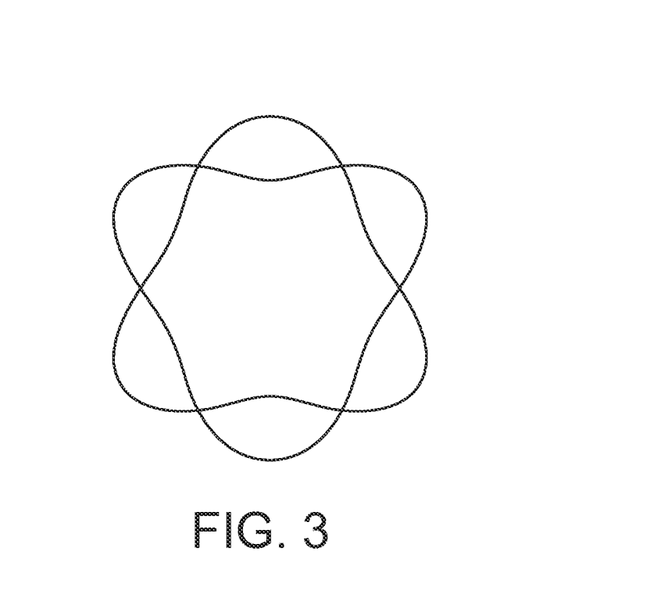
FIG. 3 shows a three-lobed radial vibration.

As is generally known, to obtain accurate density measurements, the resonant frequency used to measure the density of the fluid must be very stable. This is particularly true when the fluid comprises a gas as the resonant frequency changes by a smaller amount compared to liquid. One prior art approach to achieve the desired stability is to vibrate the vibrating member 12 in a radial vibration mode. In contrast to a bending vibration mode, for example, where the longitudinal axis of the vibrating member translates and/or rotates away from its rest position, in a radial vibration mode, the longitudinal axis of the vibrating member remains essentially stationary while at least a part of the vibrating member's wall translates and/or rotates away from its rest position. Radial vibration modes are preferred in straight conduit densitometers, such as the prior art densitometer 10 shown in FIG. 1 because radial vibration modes are self-balancing and thus, the mounting characteristics of the vibrating member are not as critical compared to some other vibration modes. One example radial vibration mode is a three-lobed radial vibration mode. An example of the change in shape of the vibrating member's wall during a three-lobed radial vibration mode is shown in FIG. 3.

If the vibrating member 12 has a perfectly round cross-sectional shape and has a perfectly uniform wall thickness, there is only one three-lobed radial vibration mode. However, due to design tolerances, this is usually impractical. Consequently, when a manufacturer attempts to make a perfectly round vibrating member 12 with a perfectly uniform wall thickness, small imperfections result in two three-lobed radial vibrations that vibrate at two different resonant frequencies, which are very close to one another. The three-lobed radial vibrational mode with the lower resonant frequency will vibrate with the peaks and valleys as shown in FIG. 3 aligned with the thinner walled portions while the higher frequency will vibrate with the peaks and valleys at the thicker wall portions. The frequency separation between the two modes is typically very small and may be less than a hertz. With two resonant frequencies so close together, a density determination is impractical because an operator will often not be able to distinguish the vibrational frequencies to determine what mode is being driven into vibration and thus, the correct density.

In some prior art densitometers, this problem is addressed by tuning the radial mode so that it has at least a minimum frequency separation between the two three-lobed radial vibrational modes as well as from the other vibrational modes, such as the two lobed modes or the four lobed modes. While the tuning can be accomplished according to a variety of techniques, one prior art approach tuning method is by grinding the vibrating member's wall in axially aligned strips so the vibrating member has different thicknesses in different circumferential regions. This is shown in FIG. 1, and in more detail in FIG. 2.

Figure 2:
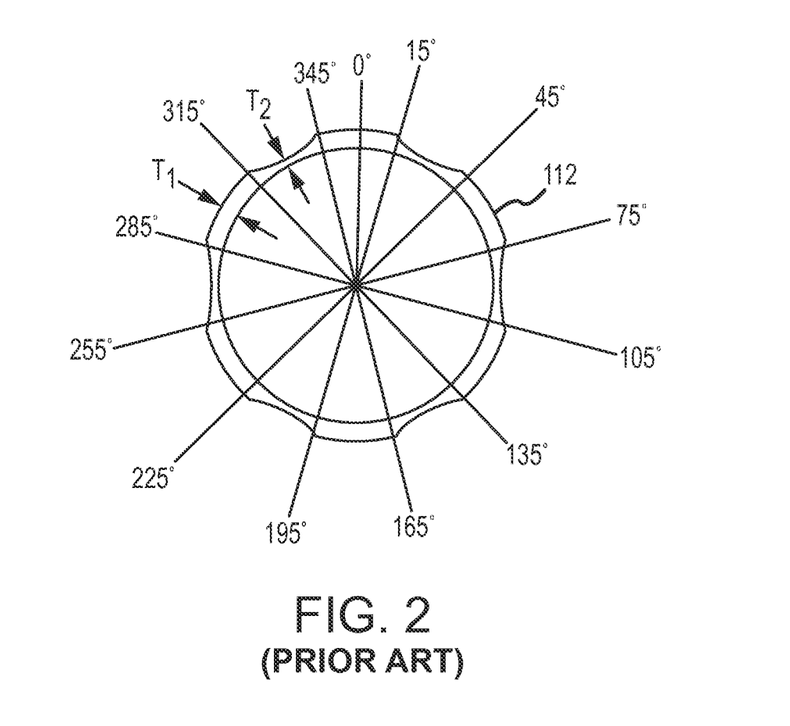
FIG. 2 shows a prior art vibrating member.

FIG. 2 shows the vibrating member 12 taken along line 2-2 of FIG. 1. FIG. 2 is shown with reference angles as well. The reference angles are taken where the driver 16 and the vibrating sensor 17 are positioned at 0°. However, the angles are merely shown as an example and other reference coordinate angles may be used.

As shown, the vibrating member 12 comprises varying wall thicknesses around the circumference of the conduit. For example, the vibrating member 12 may originally comprise a thickness $T_1$. The driver 16 and the vibrating sensor 17 are centered on one of these thick walled regions. Starting at approximately 15° and spacing uniformly around the circumference of the vibrating member 12 at approximately 30° intervals, six regions of the wall of the vibrating member 12 are ground down to a thickness $T_2$, which is less than $T_1$. Typically, the thickness of the wall is reduced by using a mandrel that has movable segments moved into position by hydraulic pressure. When the mandrel is pressurized, the movable segments move out the required amount to contact the vibrating member 12 and the thinner regions are ground. By grinding the vibrating member wall thickness in various circumferential regions, the resonant frequencies of the two three-lobed radial vibration modes are separated from one another. With the spacing between the thin regions being approximately 30°, the higher frequency three-lobed radial mode will be offset from the lower frequency three-lobed radial mode by approximately 15°. In one example, the lower frequency three-lobed vibrational mode will vibrate with the peaks and valleys centered on the thin and thick portions while the higher frequency three-lobed vibrational radial mode will have the peaks and valleys half-way between the thin and thick regions.

The above-mentioned process has several problems. The hydraulic mandrel is at the limit of its dimensional capability. In other words, the grinding needs to be extremely precise and is often close to or even beyond the design capabilities of the hydraulically operated mandrel. Further, the repeatability of the grinding operation is nearly impossible. For example, if a customer desires to have a vibrating tube with a specified resonant frequency that is also separated from the next closest mode frequency by a predetermined amount, the manufacturer must grind down the thin areas of the vibrating tube and check the frequency. If the frequencies are not as desired, further grinding is required. This process continues until the desired frequencies are achieved. However, often, during the grinding operation, the desired frequencies are jumped over due to grinding too much of the tube. The part must then be discarded and the process starts over. As can be appreciated, the grinding operation does not provide an ideal manufacturing situation.

Therefore, there exists a need for a method and apparatus for improving vibrating densitometers. Specifically, there exists a need for a vibrating densitometer with increased resonant frequency vibration mode separation while maintaining a higher product yield. The present invention solves this and other problems and an advance in the art is achieved.

SUMMARY OF THE INVENTION

A vibrating member for a vibrating densitometer is provided according to an embodiment. The vibrating member includes an inner surface with one or more arcuate portions. According to an embodiment, the inner surface further includes one or more raised portions sized and located to increase a frequency separation between a resonant frequency of a desired vibrational drive mode and a resonant frequency of one or more undesired vibrational modes.

A vibrating densitometer is provided according to an embodiment. According to an embodiment, the vibrating densitometer comprises a housing and a vibrating member located at least partially within the housing. According to an embodiment, the vibrating member comprises an inner surface with one or more arcuate portions and one or more raised portions sized and located to increase a frequency separation between a resonant frequency of a desired vibrational drive mode and a resonant frequency of one or more undesired vibrational modes.

A method for forming a vibrating densitometer including a vibrating member adapted to vibrate at one or more resonant frequencies is provided according to an embodiment. The method comprises a step of forming an inner surface of the vibrating member with one or more arcuate portions and one or more raised portions sized and located to increase a frequency separation between a resonant frequency of a desired vibrational drive mode and a resonant frequency of one or more undesired vibrational modes.

Aspects

According to an aspect, a vibrating member for a vibrating densitometer comprises:
  an inner surface including:
  one or more arcuate portions; and
  one or more raised portions sized and located to increase a frequency separation between a resonant frequency of a desired vibrational drive mode and a resonant frequency of one or more undesired vibrational modes.

Preferably, the desired drive mode comprises a first three-lobed radial vibrational mode and an undesired vibrational mode comprises a second three-lobed radial vibrational mode.

Preferably, the one or more raised portions extend an entire length of the vibrating member.

Preferably, the one or more arcuate portions comprise a first thickness, $D_1$, and the one or more raised portions comprise a second thickness, $D_2$, wherein $D_1$ is less than $D_2$.

According to another aspect, a vibrating densitometer comprises:
  a housing;
  a vibrating member located at least partially within the housing and including:
    an inner surface with one or more arcuate portions and one or more raised portions sized and located to increase a frequency separation between a resonant frequency of a desired vibrational drive mode and a resonant frequency of one or more undesired vibrational modes.

Preferably, the vibrating member comprises a first end cantilever mounted to the housing such that a second end opposite the first end is free to vibrate.

Preferably, the vibrating densitometer further comprises a driver and one or more sensors configured to vibrate the vibrating member with respect to the housing.

Preferably, the desired vibrational drive mode comprises a first three-lobed radial vibrational mode and an undesired vibrational mode comprises a second three-lobed radial vibrational mode.

Preferably, the one or more raised portions extend an entire length of the vibrating member.

Preferably, the one or more arcuate portions comprise a first thickness, $D_1$, and the one or more raised portions comprise a second thickness, $D_2$, wherein $D_1$ is less than $D_2$.

According to an aspect, a method for forming a vibrating densitometer including a vibrating member adapted to vibrate at one or more resonant frequencies comprises a step of:

forming an inner surface of the vibrating member with one or more arcuate portions and one or more raised portions sized and located to increase a frequency separation between a resonant frequency of a desired vibrational drive mode and a resonant frequency of one or more undesired vibrational modes.

Preferably, the desired vibrational drive mode comprises a first three-lobed radial vibrational mode and an undesired vibrational mode comprises a second three-lobed radial vibrational mode.

Preferably, the step of forming the inner surface comprises extending the one or more raised portions the entire length of the vibrating member.

Preferably, the step of forming the inner surface comprises forming the one or more arcuate portions with a first thickness, $D_1$, and forming the one or more raised portions with a second thickness, $D_2$, wherein $D_1$ is less than $D_2$.

Preferably, the method further comprises a step of coupling a first end of the vibrating member to a housing such that at least a portion of the vibrating member is located within the housing.

Preferably, the step of coupling comprises cantilever mounting the first end to the housing such that a second end of the vibrating member opposite the first end is free to vibrate.

Preferably, the method further comprises steps of positioning a driver and one or more vibrating sensors proximate the vibrating member to induce and sense vibrations of the vibrating member.

Preferably, the step of forming comprises cutting the one or more arcuate portions and one or more raised portions using wire electrical discharge machining.

DETAILED DESCRIPTION OF THE INVENTION

FIGS. 4-8 and the following description depict specific examples to teach those skilled in the art how to make and use the best mode of embodiments of a vibrating densitometer. For the purpose of teaching inventive principles, some conventional aspects have been simplified or omitted. Those skilled in the art will appreciate variations from these examples that fall within the scope of the present description. Those skilled in the art will appreciate that the features described below can be combined in various ways to form multiple variations of the vibrating densitometer. As a result, the embodiments described below are not limited to the specific examples described below, but only by the claims and their equivalents.

Figure 4:
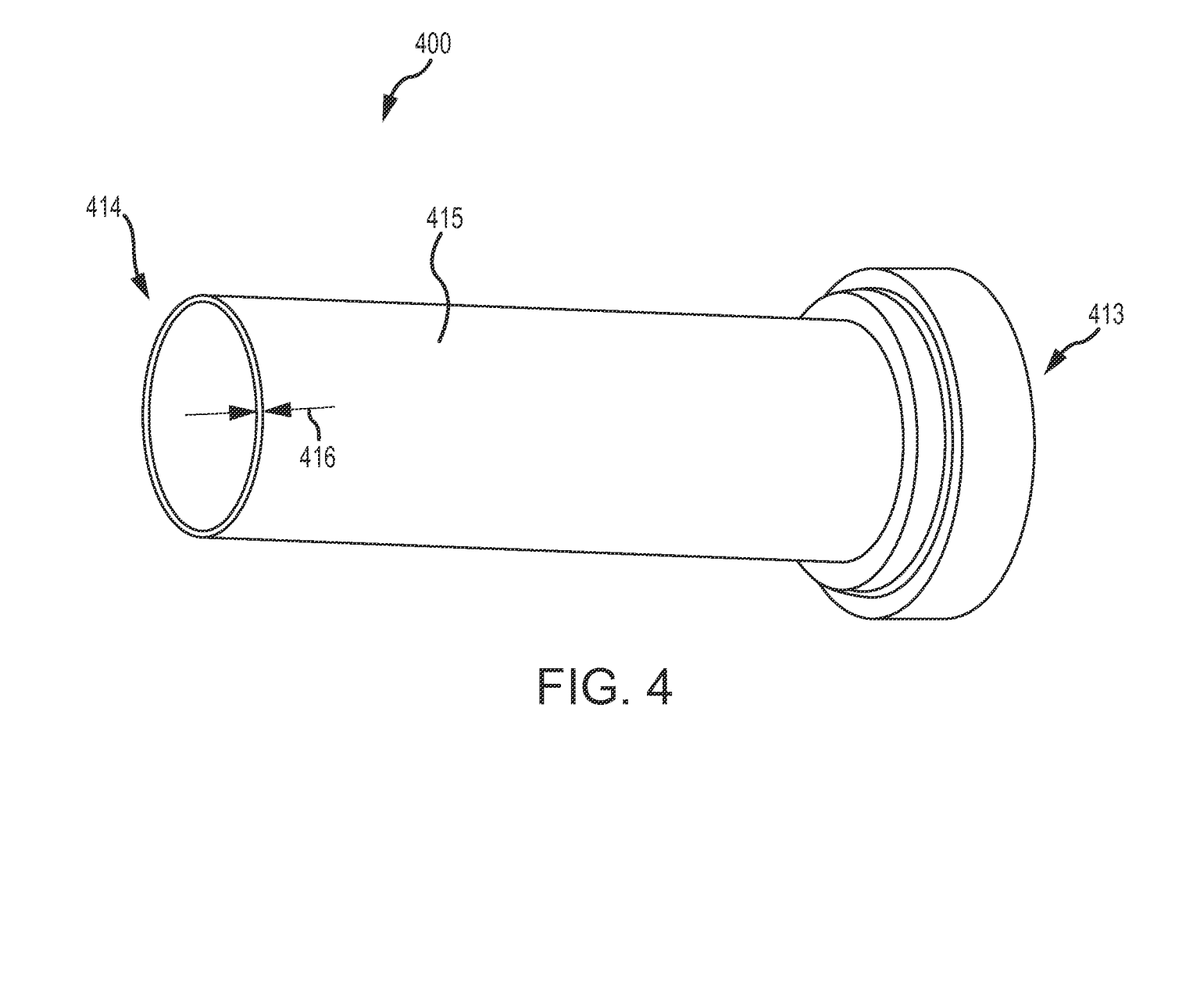
FIG. 4 shows a cylinder according to an embodiment.

FIG. 4 shows a cylinder 400 according to an embodiment. The cylinder 400 is formed as the beginning stage of a vibrating member 500 (See FIG. 5) used in a vibrating densitometer 800 (See FIG. 8). The cylinder 400 comprises an inlet end 413, which is designed to be coupled to a housing 801 to form part of the vibrating densitometer 800 and an outlet end 414, which is free to vibrate once installed in the housing 801. According to an embodiment, the cylinder 400 comprises a vibrating tube portion 415 with an approximately uniform thickness 416. The vibrating tube portion 415 is the portion of the cylinder 400 that is free to vibrate during use and is not coupled to the housing 801. The vibrating tube portion 415 comprises a generally circular outer cross-sectional surface and a generally circular inner cross-sectional surface.

As discussed above, while manufacturers attempt to create the tube portion's thickness 416 perfectly even, machine tolerances typically cannot provide perfectly even thicknesses around the entire circumference of the cylinder 400. Consequently, two or more radial modes of vibration often overlap and make density calculations impractical. Additionally, the cylinder 400 is not ready for density measurements because the average thickness 416 is greater than desired. Therefore, a thinner cylinder is desired for density measurements.

Figure 5:
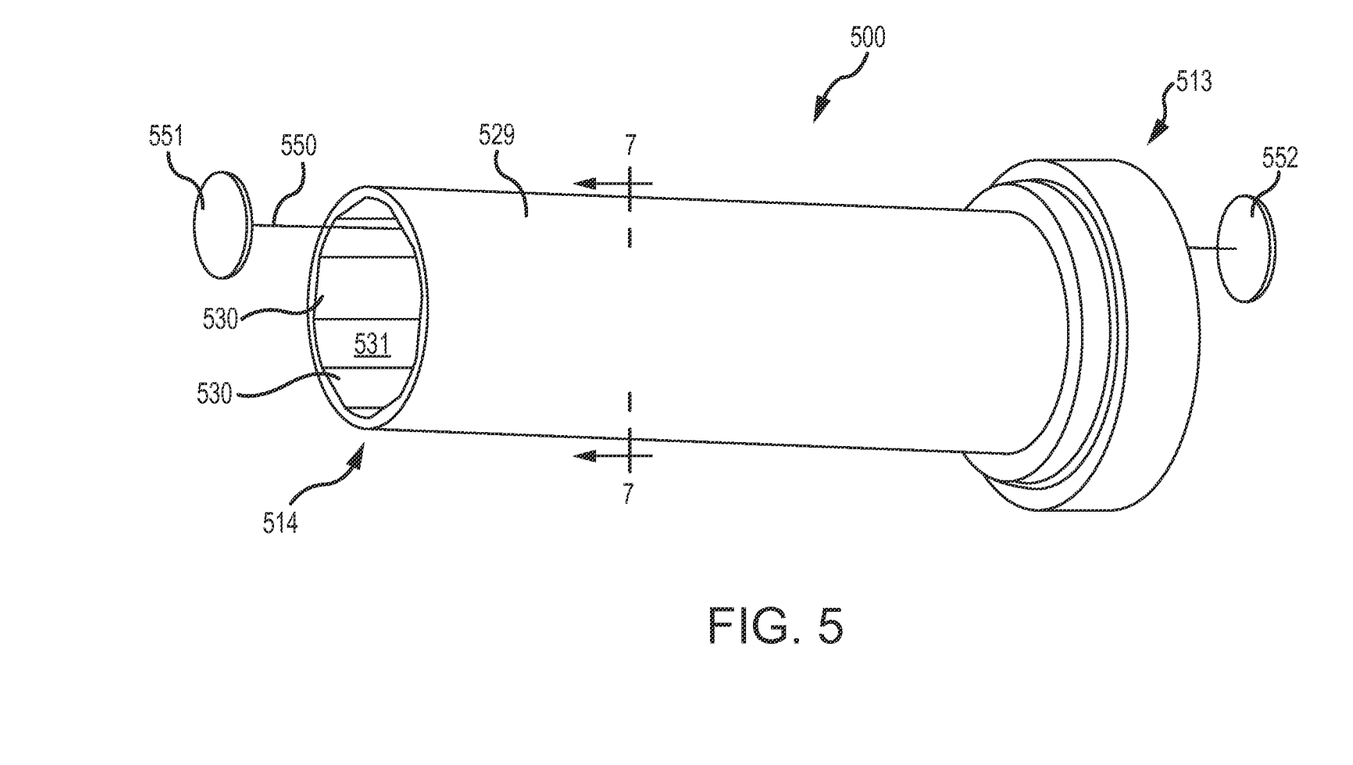
FIG. 5 shows a vibrating member for a densitometer according to an embodiment.
Figure 8:
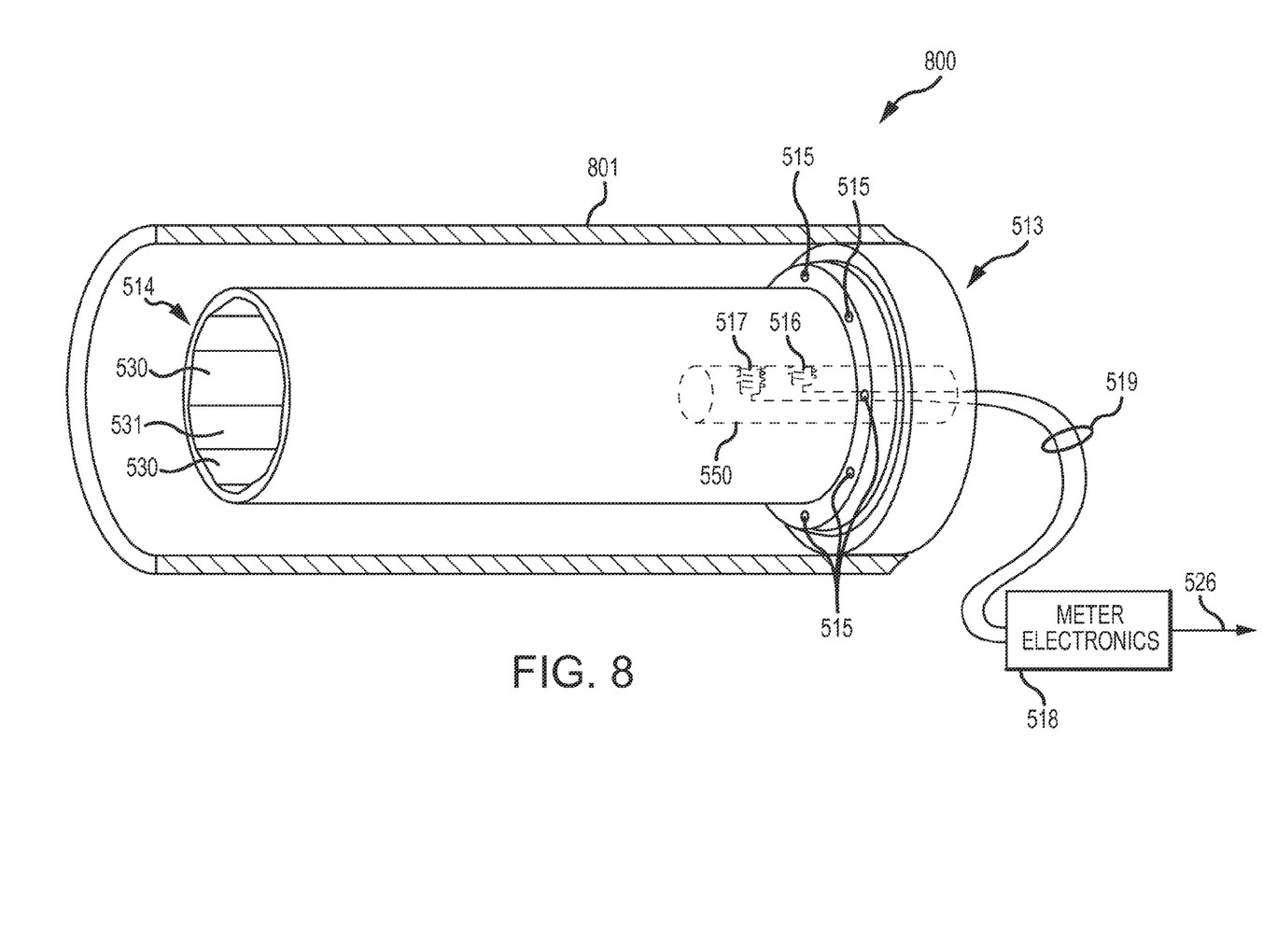
FIG. 8 shows a densitometer according to an embodiment.

FIG. 5 shows a vibrating member 500 according to an embodiment. The vibrating member 500 can be used in the vibrating densitometer 800, for example. According to an embodiment, the vibrating member 500 can be formed by removing at least a portion of the cylinder 400. It should be appreciated that while the vibrating member 500 is shown and described as being formed from the cylinder 400, the vibrating member 500 can comprise other cross-sectional shapes, such as square or rectangular, for example. According to an embodiment, an inner core 600 (See FIG. 6) is removed from the cylinder 400, thereby thinning the walls of the cylinder 400 to form the vibrating member 500.

According to an embodiment, the inner core 600 can be removed using wire electrical discharge machining (EDM). Wire EDM is generally known and can be used for repeatable cutting of various conductive materials where extreme precision is needed. Wire EDM is typically utilized where traditional cutting techniques, such as grinding, milling, drilling, etc. cannot achieve the precision or shapes desired. Although other cutting techniques may be used, wire EDM can provide extremely precise and repeatable cutting. Current cutting accuracy is known to be within 0.004 mm (0.00016 in.) with the cutting path only restricted by the diameter of the wire used.

Figure 6:
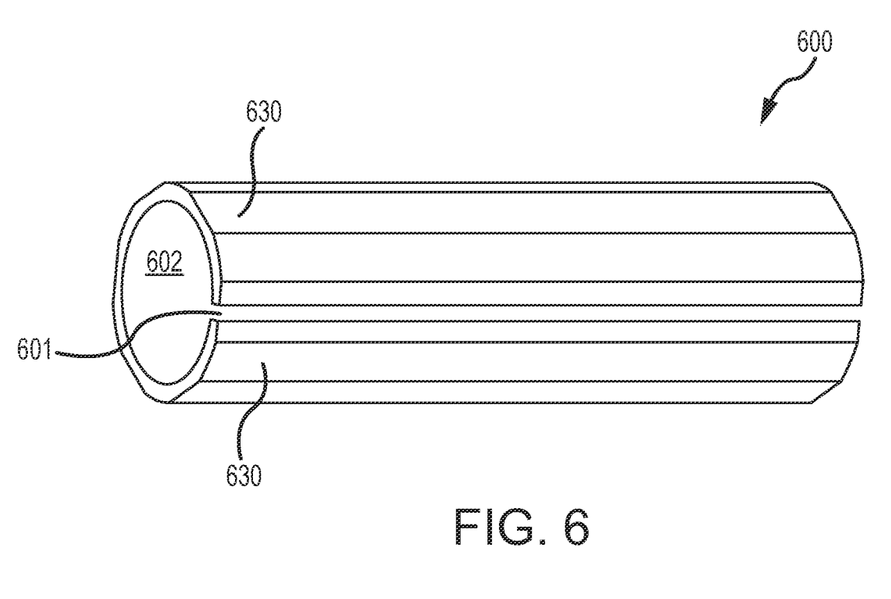
FIG. 6 shows an inner core removed from the cylinder to form the vibrating member.

With reference to FIGS. 5 & 6, according to an embodiment, the wire EDM process uses a wire 550 that is held by two guides 551, 552, which are both coupled to a controller (not shown) as is generally known in the art. Generally, the cylinder 400 and the wire 550 are immersed in a dielectric material, such as deionized water, which aids in the conductivity. With the wire 550 fed through the axial center of the cylinder 400, an inner core 600 of the cylinder 400 can be cut away by the wire 550 leaving the vibrating member 500. As can be seen in FIG. 6, the inner core 600 comprises a gap 601 where the wire 550 initially penetrates the cylinder 400 from the hollowed out center 602. The inner core 600 can be cut away due to the electrical arc between the wire 550 and the conductive material, in this case the cylinder 400 and the inner core 600. This arcing removes very small pieces of the conductive material, which are washed away with the dielectric fluid. Due, in part, to the very small pieces of the conductive material that break off at a time, very precise cuts can be made, which are typically not feasible using other cutting techniques. Often, the tolerances of the cuts are only slightly larger than the diameter of the wire 550.

As is well known, the use of wire EDM is not limited to cylindrical cutting. Rather, complex shapes can be formed using wire EDM, which can be programmed into a processing system so as to make the shapes repeatable and precise. Therefore, rather than the inner core 600 merely comprising a smaller cylinder, one or more raised portions 530 may be formed on the inner surface 531 of the vibrating member 500. According to one embodiment, the one or more raised portions 530 may extend substantially the entire length of the vibrating member 500. According to another embodiment, the one or more raised portions 530 may extend only partially along the length of the vibrating member 500. Such a configuration may be made possible by tapering the raised portions 530 where a maximum thickness of the raised portion 530 would be at the outlet end 514, for example while the raised portion 530 tapers to zero thickness as it approaches the inlet end 513, for example. It should be appreciated however, that in other embodiments, the orientation could be reversed where the maximum thickness is near the inlet end 513. However, such an orientation would limit the effectiveness of the raised portions 530 as the inlet end 513 is coupled to the housing 801 (See FIG. 8).

According to an embodiment, the one or more raised portions 530 comprise areas of increased thickness in the vibrating member 500. This can be seen better by referring to FIG. 7.

Figure 7:
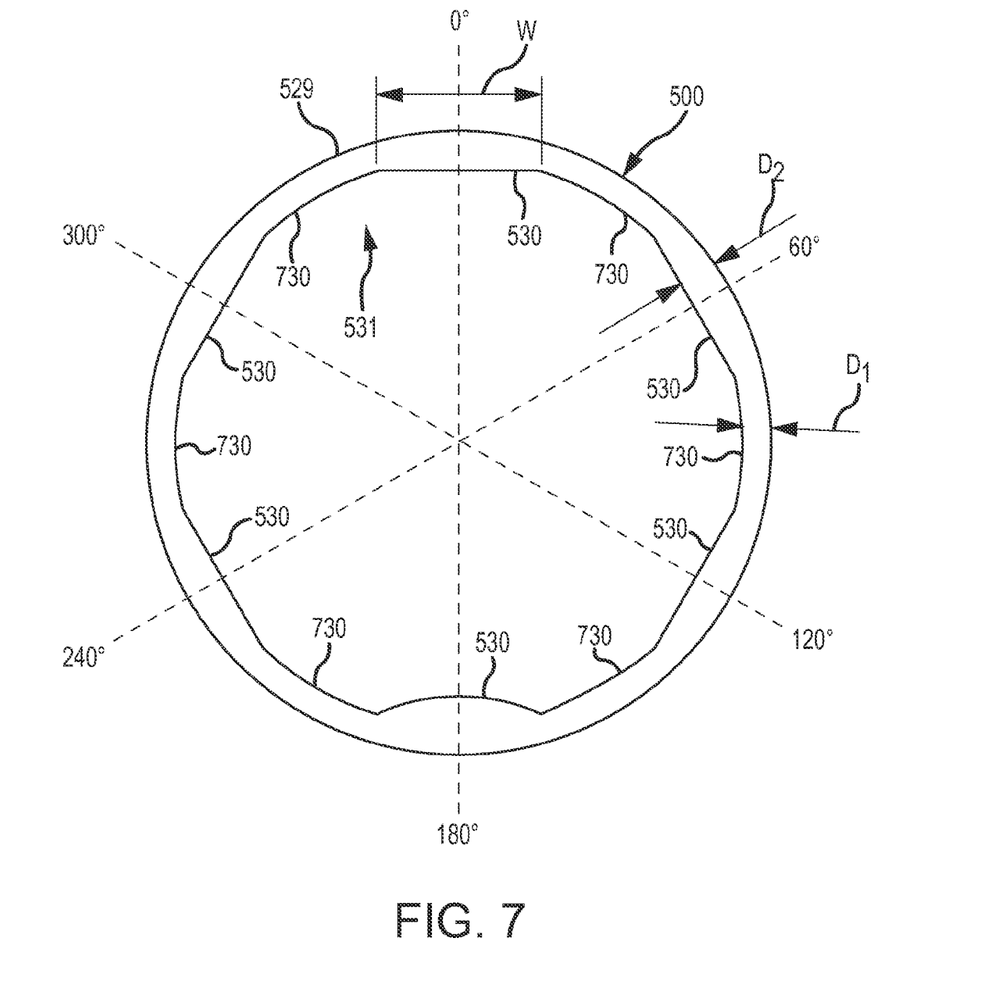
FIG. 7 shows a cross-sectional view of the vibrating member according to an embodiment.

FIG. 7 shows a cross-sectional view of the vibrating member 500 according to an embodiment taken along the line 7-7 of FIG. 5. As can be appreciated, as the wire 550 cuts away the inner core 600 from the cylinder 400, the wire 550 could travel along a generally arcuate path to form a uniform inner circumference of the vibrating member 500. However, according to an embodiment, rather than only traveling in an arcuate path, during the wire's travel around the inner surface 531 of the vibrating member 500, the wire 550 can cut out one or more raised portions 530 and one or more arcuate portions 730. In FIG. 7, six raised portions 530 are shown, which are spaced approximately 60° on center. However, in some embodiments, less than six raised portions 530 can be provided. As can be seen, the raised portions 530 comprise areas of increased thickness due to the wire 550 breaking away from the arcuate path and cutting either a straight section of the inner surface 531 of the vibrating member 500 or a projecting bump in the inner surface 531 while the outer surface 529 remains substantially cylindrically shaped (circular cross-sectional shape). The top five raised portions 530 are shown as being straight sections while the bottom raised portion 530 is shown as comprising a projecting bump that extends inward toward the radial center of the vibrating member 500. In either situation, the raised portions 530 results in the raised portions 530 comprising a width, w and a maximum thickness of $D_2$ whereas the arcuate portions 730 of the vibrating member 500 comprise an average thickness of $D_1$, which is less than $D_2$. According to an embodiment, the raised portions 530 can be sized and located to increase a frequency separation between a resonant frequency of the desired drive mode vibration and a resonant frequency of at least a second vibrational mode. As discussed above, as one example, the raised portions 530 can be sized and located to increase a frequency separation between the lower frequency three-lobed radial mode and the higher frequency three-lobed radial mode. The size and location of the raised portions 530 can be determined during an initial testing procedure or using finite element analysis, for example.

As can be seen in FIG. 6, the divergence from the arcuate path is also visible on the outer surface of the inner core 600 as flat portions 630. It should be appreciated that the widths and thicknesses of the raised portions 530 and the flat portions 630 are not drawn to scale in the figures. The particular sizes of the raised portions 530 and flat portions 630 may vary and in some embodiments are so small that they may barely be visible to the human eye. Therefore, the sizes of the components shown in the figures should in no way limit the scope of the present embodiment.

According to an embodiment, the raised portions 530, which result in increased thickness of the vibrating member 500, can separate an intended drive mode frequency from one or more undesired vibrational mode frequencies. For example, the one or more raised portions 530 and the one or more arcuate portions 730 can separate the lower frequency three-lobed radial vibration mode from the higher frequency three-lobed radial vibration mode. The increased thickness, $D_2$, of the raised portions 530 can center the peaks and valleys of the lower frequency three-lobed radial vibration mode on the raised portions 530 while the higher frequency three-lobed radial vibration mode will have peaks and valleys midway between the centers of the raised portions 530 and the arcuate portions 730. According to an embodiment, the width, w, and the thickness, $D_2$, can be adjusted to provide the desired frequency separation. According to an embodiment, the frequency separation between the intended drive mode and unintended modes will be at least a threshold amount. For example, some embodiments may require that the lower frequency three-lobed radial vibration mode is separated from the next closest vibration mode by at least 10 Hz. It should be appreciated however, that 10 Hz. is merely one example and the particular frequency separation will vary from one application to another and should in no way limit the claims that follow.

FIG. 8 shows a vibrating densitometer 800 according to an embodiment. The vibrating densitometer 800 may be configured to determine a density of a fluid, such as a gas, a liquid, a liquid with entrained gas, a liquid with suspended particulates, or a combination thereof. Due to viscous damping, the vibrating densitometer 800 is typically used to measure a density of a gas rather than a density of a liquid.

According to an embodiment, the vibrating densitometer 800 includes the vibrating member 500 including the one or more raised portions 530 and the one or more arcuate portions 730 formed on the inner surface 531. As shown in FIG. 8, the inlet end 513 can be coupled to the housing 801 while the outlet end 514 is free to vibrate. Further visible in FIG. 8 are a plurality of apertures 515, which can provide fluid communication paths for the fluid under test to reach the outer surface of the vibrating member 500. It should be appreciated that the apertures 515 are optional.

According to an embodiment, the vibrating densitometer 800 can further include one or more drivers 516 and one or more vibrating sensors 517, which can be coupled to a central tower 550. The driver 516 can be adapted to vibrate the vibrating member 500 in one or more vibrational modes. While the driver 516 is shown located within a central tower 550 positioned within the vibrating member, in some embodiments, the driver 516 is positioned between the housing 801 and the vibrating member 500, for example. Furthermore, it should be appreciated that while the driver 516 is shown positioned closer to the first end 513, the driver 516 may be positioned at any desired location. According to an embodiment, the driver 516 can receive an electrical signal from the meter electronics 518 via leads 519. According to one embodiment, the driver 516 can be centered on one of the raised portions 530, for example.

According to an embodiment, the vibrating densitometer 800 can also include a vibrating sensor 517. While the vibrating sensor 517 is shown coaxially aligned with the driver 516, in other embodiments, the vibrating sensor 517 may be coupled to the vibrating member 500 in other locations. The vibrating sensor 517 can transmit a signal to the meter electronics 518 via lead 519. The meter electronics 518 can process the signals received by the vibrating sensor 517 to determine a resonant frequency of the vibrating member 500. If a fluid under test is present, the resonant frequency of the vibrating member 500 will change inversely proportional to the fluid density as is known in the art. The proportional change may be determined during an initial calibration, for example. In the embodiment shown, the vibrating sensor 517 also comprises a coil. The vibrating sensor 517 is similar to the driver 516; however, while the driver 516 receives a current to induce a vibration in the vibrating member 500, the vibrating sensor 517 uses the motion of the vibrating member 500 created by the driver 516 to induce a voltage. Coil drivers and sensors are well known in the art and a further discussion of their operation is omitted for brevity of the description. Furthermore, it should be appreciated that the driver 516 and the vibrating sensor 517 are not limited to coils, but rather may comprise a variety of other well-known vibrating components, such as piezo-electric sensors, for example. Therefore, the present embodiment should in no way be limited to coils. Furthermore, those skilled in the art will readily recognize that the particular placement of the driver 516 and sensor 517 can be altered while remaining within the scope of the present embodiment.

The embodiments described above provide a vibrating member 500 for a vibrating densitometer 800, which improves the frequency separation between a desired drive mode resonant frequency and one or more undesired frequencies. In the example provided, the desired drive mode frequency comprises the three-lobed radial mode vibrational frequency; however, the embodiments are equally applicable to other vibrational modes. Unlike prior art vibrating members, which grind the outer surface of the vibrating member in an attempt to achieve frequency separation, the embodiments described above precisely cut one or more raised portions 530 into an inner surface 531 of the vibrating member 500. Therefore, while the outer surface 529 remains substantially cylindrically shaped, the inner surface 531 comprises one or more raised portions 530 and one or more arcuate portions 730. The one or more raised portions 530 can be sized and located to separate the drive frequency from one or more undesired frequencies as discussed above.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other vibrating members, and not just to the embodiments described above and shown in the accompanying figures. Accordingly, the scope of the embodiments described above should be determined from the following claims.

We claim:

1. A vibrating member (500) for a vibrating densitometer (800), comprising:
   an inner surface (531) including:
      one or more arcuate portions (730); and
      one or more raised portions (530) sized and located to increase a frequency separation between a resonant frequency of a desired vibrational drive mode and a resonant frequency of one or more undesired vibrational modes.

2. The vibrating member (500) of claim 1, wherein the desired drive mode comprises a first three-lobed radial vibrational mode and an undesired vibrational mode comprises a second three-lobed radial vibrational mode.

3. The vibrating member (500) of claim 1, wherein the one or more raised portions (530) extend an entire length of the vibrating member (500).

4. The vibrating member (500) of claim 1, wherein the one or more arcuate portions (730) comprise a first thickness, $D_1$, and the one or more raised portions (530) comprise a second thickness, $D_2$, wherein $D_1$ is less than $D_2$.

5. A vibrating densitometer (800), comprising:
   a housing (801);
   a vibrating member (500) located at least partially within the housing (801) and including:
      an inner surface (531) with one or more arcuate portions (730) and one or more raised portions (530) sized and located to increase a frequency separation between a resonant frequency of a desired vibrational drive mode and a resonant frequency of one or more undesired vibrational modes.

6. The vibrating densitometer (800) of claim 5, wherein the vibrating member (500) comprises a first end (513) cantilever mounted to the housing (801) such that a second end (514) opposite the first end (513) is free to vibrate.

7. The vibrating densitometer (800) of claim 5, further comprising a driver (516) and one or more sensors (517) configured to vibrate the vibrating member (500) with respect to the housing (801).

8. The vibrating densitometer (800) of claim 5, wherein the desired vibrational drive mode comprises a first three-lobed radial vibrational mode and an undesired vibrational mode comprises a second three-lobed radial vibrational mode.

9. The vibrating densitometer (800) of claim 5, wherein the one or more raised portions (530) extend an entire length of the vibrating member (500).

10. The vibrating densitometer (800) of claim 5, wherein the one or more arcuate portions (730) comprise a first thickness, $D_1$, and the one or more raised portions (530) comprise a second thickness, $D_2$, wherein $D_1$ is less than $D_2$.

11. A method for forming a vibrating densitometer including a vibrating member adapted to vibrate at one or more resonant frequencies, comprising a step of:
  forming an inner surface of the vibrating member with one or more arcuate portions and one or more raised portions sized and located to increase a frequency separation between a resonant frequency of a desired vibrational drive mode and a resonant frequency of one or more undesired vibrational modes.

12. The method of claim 11, wherein the desired vibrational drive mode comprises a first three-lobed radial vibrational mode and an undesired vibrational mode comprises a second three-lobed radial vibrational mode.

13. The method of claim 11, wherein the step of forming the inner surface comprises extending the one or more raised portions the entire length of the vibrating member.

14. The method of claim 11, wherein the step of forming the inner surface comprises forming the one or more arcuate portions with a first thickness, $D_1$, and forming the one or more raised portions with a second thickness, $D_2$, wherein $D_1$ is less than $D_2$.

15. The method of claim 11, further comprising a step of coupling a first end of the vibrating member to a housing such that at least a portion of the vibrating member is located within the housing.

16. The method of claim 15, wherein the step of coupling comprises cantilever mounting the first end to the housing such that a second end of the vibrating member opposite the first end is free to vibrate.

17. The method of claim 11, further comprising steps of positioning a driver and one or more vibrating sensors proximate the vibrating member to induce and sense vibrations of the vibrating member.

18. The method of claim 11, wherein the step of forming comprises cutting the one or more arcuate portions and one or more raised portions using wire electrical discharge machining.

* * * * *